United States Patent

Suzuki et al.

[11] Patent Number: 5,231,576
[45] Date of Patent: Jul. 27, 1993

[54] MEASURING APPARATUS

[75] Inventors: Yoshiro Suzuki, Yamanashi; Noriyuki Kurihara, Chigasaki, both of Japan

[73] Assignees: Terumo Kabushiki Kaisha; Yamatake-Honeywell Co., Ltd., both of Tokyo, Japan

[21] Appl. No.: 578,577

[22] Filed: Sep. 7, 1990

[30] Foreign Application Priority Data

Sep. 8, 1989 [JP] Japan ................. 1-231546

[51] Int. Cl.⁵ .................. G06F 15/00; G01J 3/42; G01J 3/52; A61B 5/02
[52] U.S. Cl. .................. 364/413.09; 364/413.02; 364/413.08; 356/325; 356/422; 356/423; 128/677
[58] Field of Search ............. 364/497, 413.09, 413.02; 356/184; 128/677, 662.05, 664, 672

[56] References Cited

U.S. PATENT DOCUMENTS

| | | | |
|---|---|---|---|
| 3,833,864 | 7/1974 | Kiess et al. | 356/184 |
| 4,171,913 | 10/1979 | Wildy et al. | 364/497 |
| 4,407,959 | 10/1983 | Tsuji et al. | 364/413.09 |
| 4,420,564 | 12/1983 | Tsuji et al. | 364/413.09 |
| 4,731,726 | 3/1988 | Allen, III | 364/416 |
| 4,871,258 | 10/1989 | Herpichboehm et al. | 364/413.09 |
| 5,016,283 | 5/1991 | Bacus et al. | 364/413.08 |

FOREIGN PATENT DOCUMENTS 256806 2/1988 European Pat. Off. .
290013 9/1988 European Pat. Off. .
63-282620 11/1988 Japan .

OTHER PUBLICATIONS

Patent Abstracts of Japan vol. 13, No. 102 (P-841) Mar. 10, 1989.

*Primary Examiner*—Roy N. Envall, Jr.
*Assistant Examiner*—Khai Tran
*Attorney, Agent, or Firm*—Burns, Doane, Swecker & Mathis

[57] ABSTRACT

The present invention is an apparatus for measuring the constituent concentration of a specimen on the basis of the color change in a test material housed in a test piece, which has reacted because of the specimen. The apparatus irradiates the test material which is a test piece loaded in the apparatus's main body and detects the intensity of the light reflected by the test material. A detection signal detected in the above way is sampled in a time period before and after the measurement timing at which the test material changes in color because of the specimen. An average value of the sampled detection signals is determined. The constituent concentration of the specimen is computed by referring to a stored conversion table on the basis of the average value determined in the above way.

14 Claims, 9 Drawing Sheets

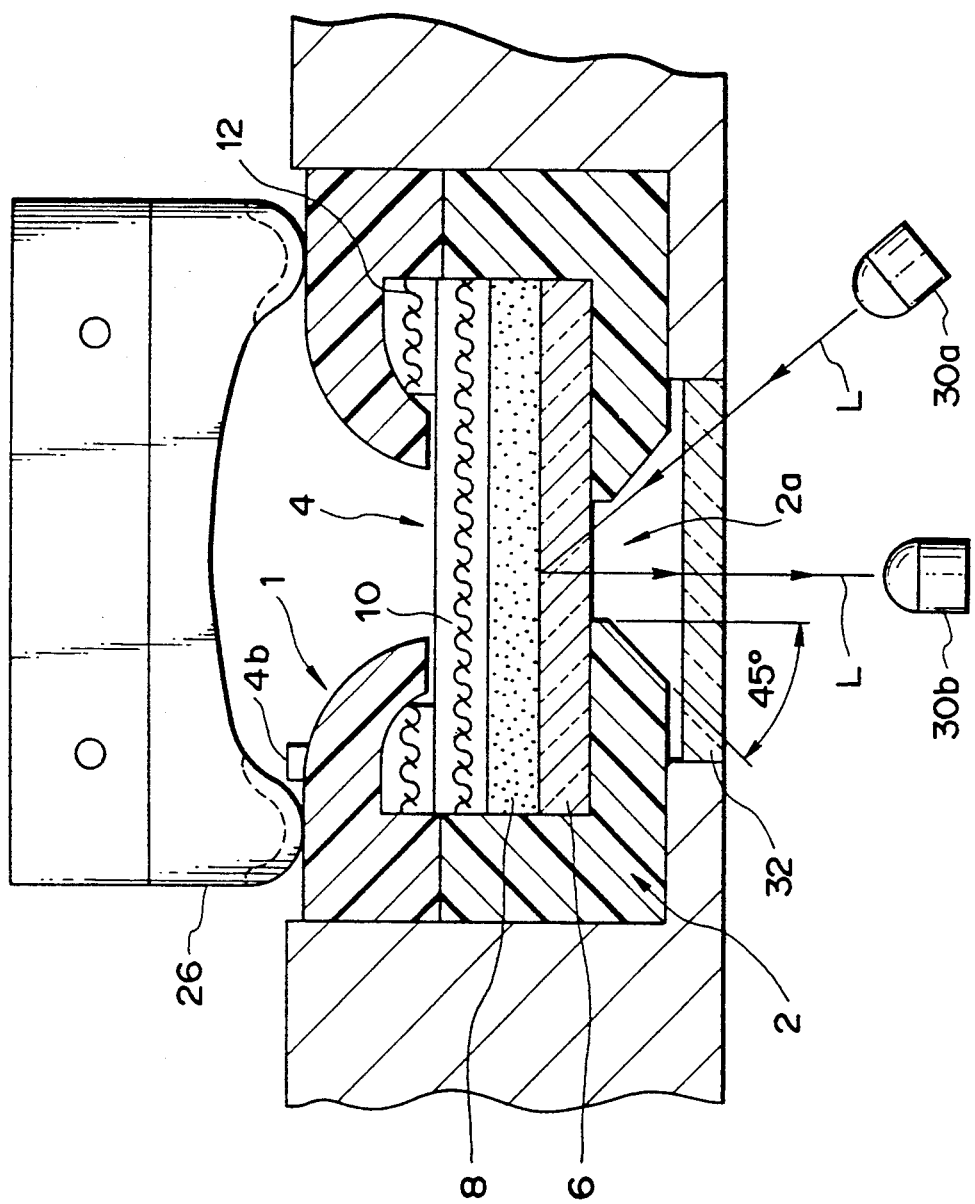
F I G. 4

MEASURING APPARATUS

BACKGROUND OF THE INVENTION

1. Field of the Invention

The present invention relates to a measuring apparatus which measures the concentration of a specimen after the specimen to be measured is applied to a test material of a test piece and the test piece is loaded and, in particular, to a measuring apparatus that measures humor of a living body.

2. Description of the Related Art

In a conventional biochemical measuring device, particularly a blood sugar measuring device, after blood to be measured is applied to a test piece and after the lapse of a predetermined time until test paper disposed on the test piece has reacted to the blood, the concentration of the reaction color of the test paper is photoelectrically read out in one measurement. The blood sugar value of the blood is determined on the basis of the concentration value.

At this point, in reading out the reaction color of the test paper, when an analog signal corresponding to the intensity of the light reflected of the light with which the test piece is irradiated is output so that the analog signal is input after it is converted into a digital signal, a corresponding blood sugar value is determined. The A/D conversion and digital input of this analog signal is performed at a predetermined time (for example, after one minute) from the time the blood is applied to the test piece. In the prior art, after a lapse of this predetermined time, only a sampling value of one time is converted into a digital signal and is input.

Digital values which have been converted from analog to digital show discrete step-like values in accordance with the resolution of an A/D converter. Accordingly, the measurement results become discrete step-like values, and thus A/D conversion discrepancies are caused with respect to true analog values. Also, errors caused by intermittently generated noise become large enough not to be ignored when the noises are caused simultaneously at one sampling time.

SUMMARY OF THE INVENTION

The present invention has been devised in light of the above-mentioned examples of the prior art. An object of the present invention is to provide a measuring apparatus which is capable of measuring the concentration of the constituents of a specimen with a high degree of accuracy.

Another object of the present invention is to provide a measuring apparatus which is capable of determining the concentration of a specimen with high accuracy, with small A/D conversion discrepancies and a small amount of noise influence.

In order to achieve the above-mentioned objects, the measuring apparatus of the present invention, that is, a measuring apparatus in which a test piece to which a specimen is applied is loaded, that measures the concentration of the specimen on the basis of the difference in color of a test material which is housed in said test piece and which has reacted because of said specimen, comprises an irradiation device for irradiating the test material; a detection device for detecting the intensity of the light reflected by the test material and outputting a corresponding analog signal; a digital conversion device for sampling an analog signal and converting it into a digital signal at a predetermined cycle, in a time period before and after the measurement timing; and a computation device for computing an average value of the digital signals at the above time interval and determining the constituent concentration of the specimen by referring to a conversion table on the basis of the average value.

In order to achieve the above-mentioned objects, the measuring apparatus of the present invention, that is, a measuring apparatus in which a test piece to which a specimen is applied is loaded, that measures the concentration of the specimen on the basis of the difference in color of a test material which is housed in the test piece and which has reacted because of the specimen, comprises; irradiation means for irradiating the test material; detection means for detecting the intensity of the light reflected by the test material and outputting a corresponding analog signal; digital conversion means for sampling the analog signal and converting it into a digital signal at a predetermined cycle, in a time period before and after the measurement timing; and computation means for computing an average value of the digital signals in the time period and determining the constituent concentration of the specimen by referring to a stored conversion table on the basis of the average value.

In order to achieve the above-mentioned objects, the measuring apparatus of the present invention, that is, a measuring apparatus in which a test piece to which a specimen is applied is loaded, that measures the concentration of the specimen on the basis of the difference in color of a test material which is housed in the test piece and which has reacted because of the specimen, comprises; loading detection means for detecting whether the test piece is loaded; irradiation means for irradiating the test material in a time period before and after the measurement timing at which the test material changes in color because of specimen, after the loading of the test piece is detected by means of the loading detection means; intensity detection means for detecting the intensity of the light reflected by the test material and outputting a corresponding analog signal; digital conversion means for sampling the analog signal, and converting it into a digital signal at a predetermined cycle, in a time period with equal periods before and after the measurement timing; computation means for computing an average measurement value at the measurement timing by computing the average value of the digital signals at the time period with equal periods before and after the measurement timing, the sections of which period before and after the measurement timing are equal; and arithmetic operation means for determining the constituent concentration of the specimen by referring to a stored conversion table on the basis of said average measurement value.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 4 is a view illustrating the cross section taken along the line A—A' of FIG. 3 in a state in which the test piece is loaded;

DESCRIPTION OF THE PREFERRED EMBODIMENTS

The preferred embodiments of the present invention will be explained in detail hereinafter with reference to the accompanying drawings.

Figure 1:
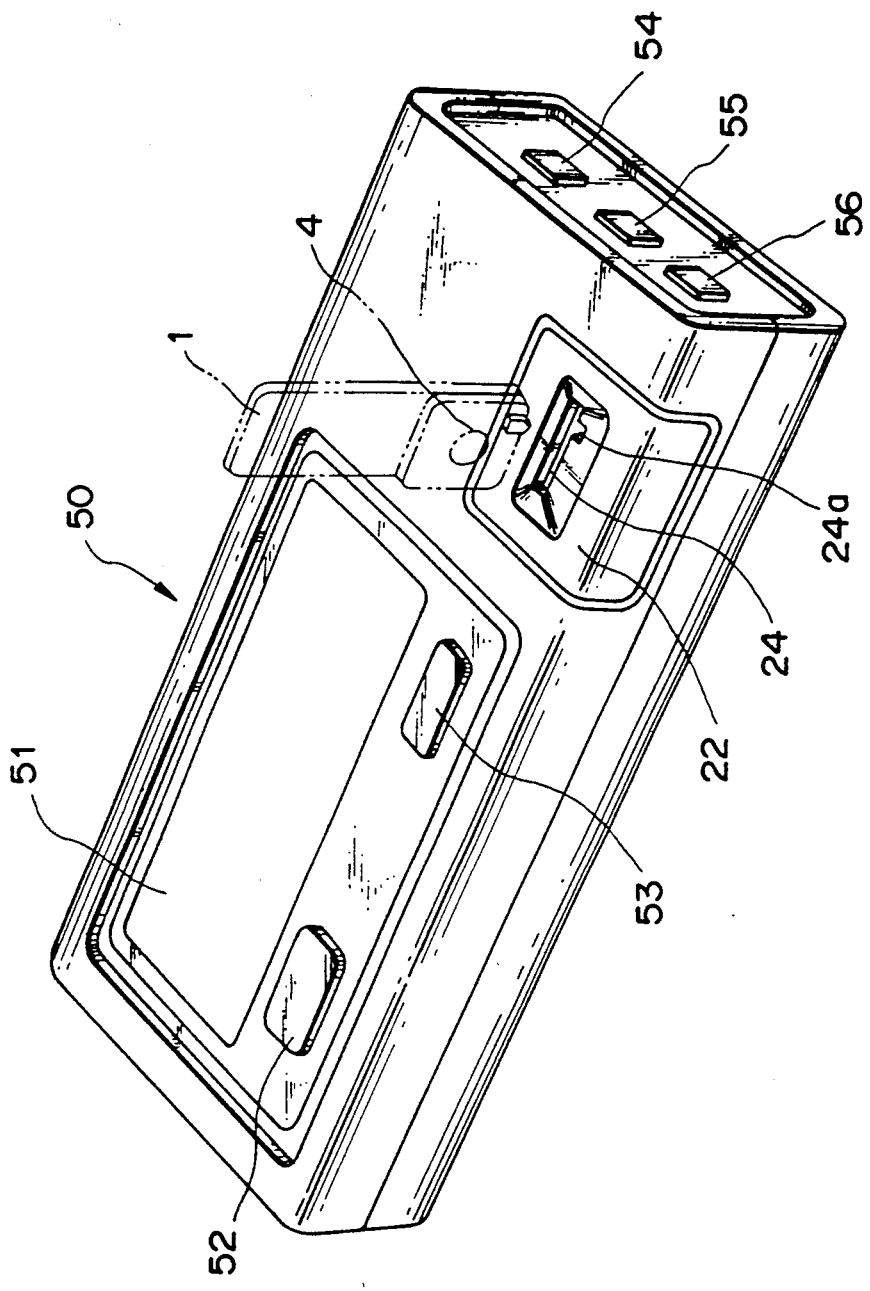
FIG. 1 is an external perspective view of the exterior of an automatic blood sugar measuring device of this embodiment.

FIG. 1 is a perspective view of the exterior of an automatic blood sugar measuring device 50 of this embodiment.

In FIG. 1, numeral 50 denotes the main body of the automatic blood sugar measuring device, 51 denotes a liquid-crystal display section for displaying measurement results, and 52 denotes a power-supply switch. The power supply of the device 50 is turned on by depressing this switch 52 when the power supply of the device 50 is off. Conversely, the power supply of the device 50 is turned off by depressing this switch 52 when the power supply of the device 50 is on. Numeral 53 denotes a storage retrieval switch. Each time the switch 53 is depressed, measurement results stored in a memory (a RAM 74 in FIG. 2) contained in the device are read out in sequence along with measurement day and time, and are displayed on a display section 51. Numeral 1 denotes a blood sugar test piece. Blood to be measured is applied to a test paper part in the test piece 1 through the opening 4 for the test piece 1. The test piece 1 is inserted and loaded into an opening (insertion hole) 24 of the device 50, then the blood sugar value of the applied blood is measured.

Numeral 54 denotes a storage stop switch. During the measurement of a blood sugar value, when the switch 54 is not pressed within a predetermined time period after measurement, the measured blood sugar value is automatically stored in the memory (the RAM 74). However, by pressing this switch 54 within the predetermined time period after measurement, it is possible that the blood sugar value measured immediately before is not stored in the memory (the RAM 74). Thus, for example, when the application of blood to test paper is poor, or when abnormal measurement values are obtained due to operation errors, it is possible that the values are not stored in the memory (the RAM 74).

Numeral 55 denotes a setting switch. By pressing this switch 55, the values of (month, day, hour, and minute) can be set and stored in the RAM 74. Numeral 56 denotes a change switch which can change a day or time updated from the instruction by means of the setting switch 55. [Explanation of the construction of the device (FIG. 2)]

Figure 2:
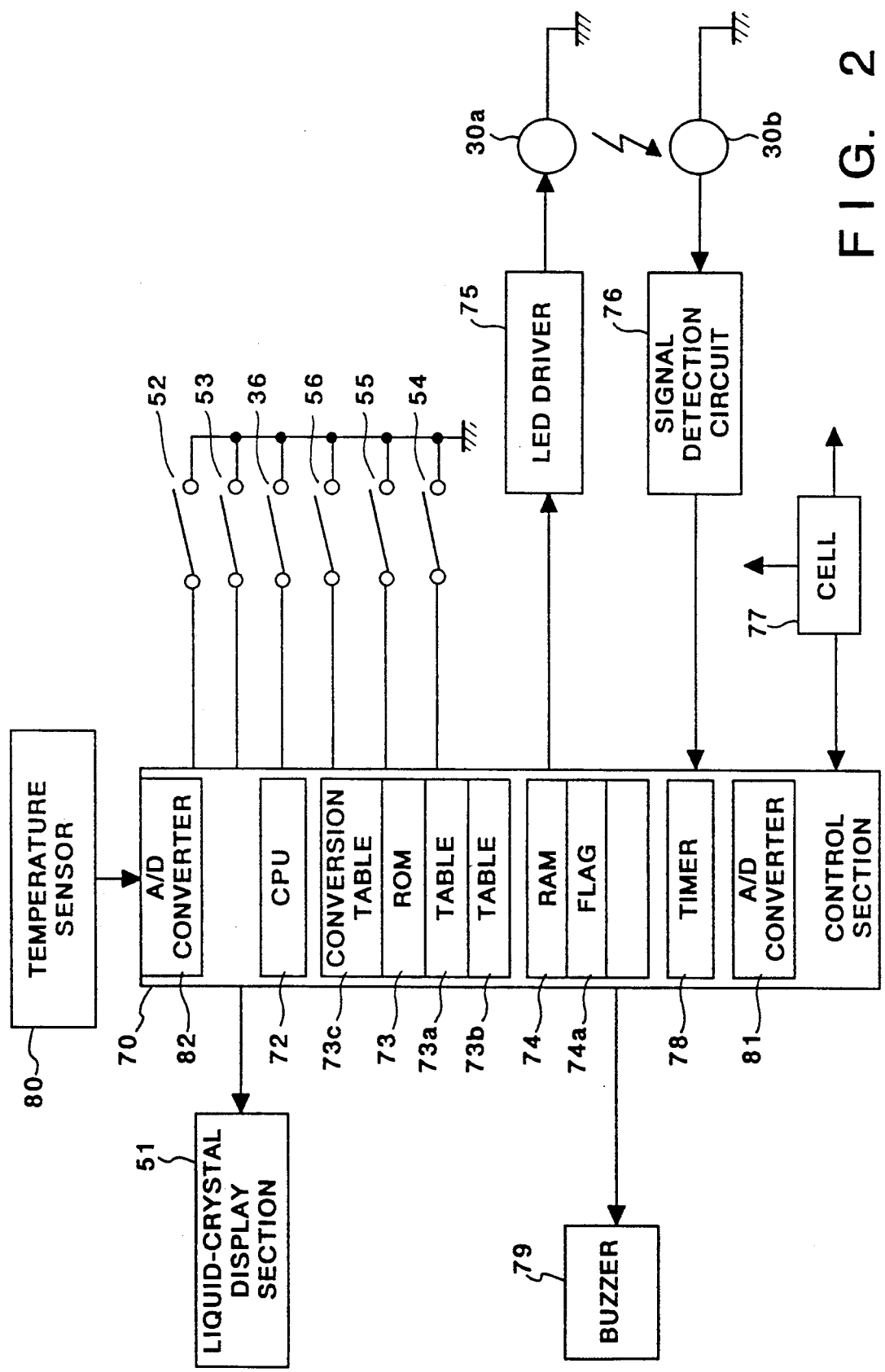
FIG. 2 is a block diagram illustrating the construction of the automatic blood sugar measuring apparatus.

FIG. 2 is a block diagram illustrating the construction of the automatic blood sugar measuring device 50. Parts common to those of FIG. 1 are given the same numerals, and the explanation thereof is omitted.

In FIG. 2, numeral 70 denotes a control section which controls the whole device. This control section comprises a CPU 72 such as a microprocessor, a ROM 73 in which are stored control programs for the CPU 72 shown in the flowcharts of FIGS. 5 to 7 and various kinds of data, and a RAM 74 which is used as a work area for the CPU 72 and in which measurement results are stored along with the measurement day and time. The control section 70 accepts, as input, the status of various kinds of connected switches in order to perform an operation corresponding to these inputs. It in turn obtains a blood sugar value by reading out a signal value from a photosensor 30b, and causes the liquid-crystal display section 51 to display measurement results and the contents of the memory (the RAM 74). Numeral 36 denotes a switch for detecting whether the test piece 1 is inserted into the opening 24. The switch is turned on when the test piece 1 is inserted, thus causing the measurement of a blood sugar value to be started automatically when the power supply of the device 50 is on.

Numeral 75 denotes an LED driver which causes an LED 30a to go on at a constant current when instructions are received from the control section 70. The LED 30a irradiates the test piece 1 from the rear side (the rear side of the test piece 1 shown in FIG. 1). The reflected light is detected by means of the photosensor 30b, and the blood sugar value of the blood of the test piece 1 is determined on the basis of the intensity of the reflected light. Numeral 76 denotes a signal detection circuit for converting the intensity of the reflected light, which is detected by the photosensor 30b, into a voltage value. An analog signal from the signal detection circuit 76 is input to the control section 70 and is converted from analog to digital by means of an A/D converter 81. A digital signal corresponding to the reflected light intensity is then input to the CPU 72.

Numeral 77 denotes a cell as a power supply which supplies power to the whole device 50. Numeral 78 denotes a timer disposed in the control section 70, which measures the lapse of time and measures a predetermined time by the instruction from the CPU 72. Numeral 79 denotes a buzzer which sounds an alarm to operators and posts a lapse of one second, a measurement termination, and errors, during the count-down display which will be described later. Numeral 80 denotes a temperature sensor that measures the ambient temperatures in which the automatic blood sugar measuring device 50 is placed and inputs it to the control section 70 in the form of an analog signal. This analog signal is converted from analog to digital by means of the A/D converter 82 and is input to the CPU 72. This temperature signal is used to compensate the reflected light intensity to be described later. [Explanation of the insertion section to which a test piece is inserted (FIGS. 3 and 4)]

Figure 3:
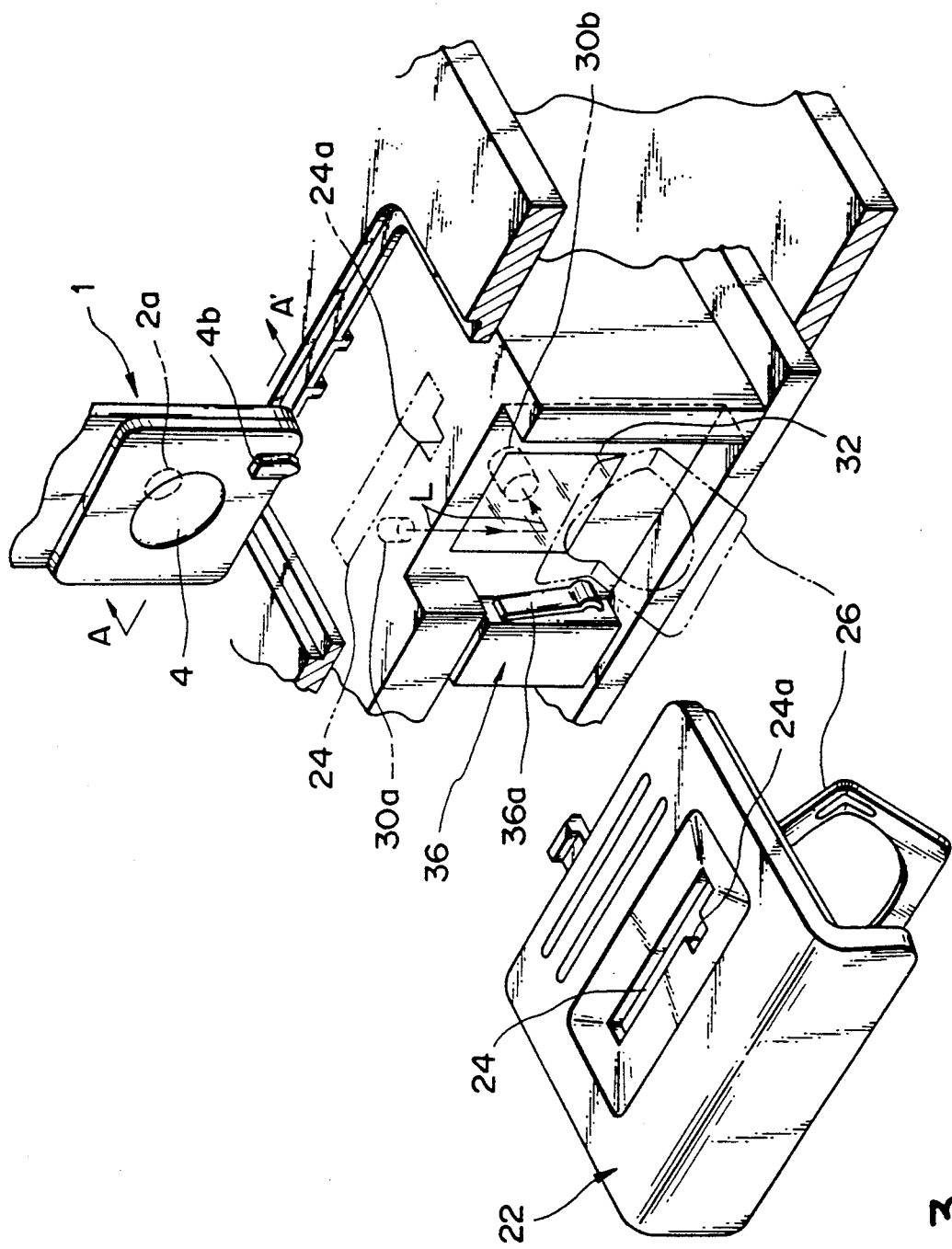
FIG. 3 is an external perspective view illustrating the details of a loading section into which a test piece is to be loaded.

FIG. 3 is an external perspective view illustrating the details of the insertion section of the automatic blood sugar measuring device 50 of the embodiment, into which a test piece is to be inserted. The same parts as those shown in the above-mentioned figures are given the same numerals.

FIG. 3 shows a state in which an auxiliary cover 22 is removed from the device's main body 50 shown in FIG. 1. The portions indicated by the dotted lines of the opening 24 and a spring 26, which depresses the test piece 1, show positions of respective sections in a state in which the auxiliary cover 22 is mounted. A projection 4b provided in the test piece 1 is engaged with the notch 24a in the opening 24 of the device 50 for the purpose of preventing a reverse insertion of the test piece 1. The test piece 1 inserted and loaded in the device 50 is depressed in the direction parallel to a light-transmissive body 32 by means of a spring 26. Light L emitted from the LED (light-emitting diode) 30a irradiates the opening 2a of the test piece 1 through the light-transmissive body 32, and the reflected light reaches the photosensor 30b. This construction will be explained in detail with reference to FIG. 4.

Numeral 36 denotes a microswitch for detecting whether the test piece 1 is loaded. At the time the test piece 1 is loaded, an actuator 36a of the microswitch 36 is depressed by the side of the test piece 1, causing the microswitch to be turned on. As a result, the control section 70 accepts a signal from this switch 36, with the result that whether the test piece 1 has been loaded in the device 50 can be detected. Since this actuator 36a does not turn on the switch 36 as long as the test piece 1 is not mounted normally, a defective loading of the test piece 1 can be detected by a signal from the switch 36.

FIG. 4 is a transverse sectional view of the measuring section illustrating a state taken along the line A—A' of FIG. 3 in which the test piece 1 is mounted on the device 50.

Blood applied through the opening 4 of the test piece 1 oozes out in a liquid spreading layer 10 and infiltrates in a reagent layer (test paper) 8. Numeral 12 denotes a liquid absorbing layer for absorbing excess blood which is not absorbed in the liquid spreading layer 10. Numeral 6 denotes a light-transmissive layer for transmitting light. Light L emitted from the LED 30a passes through the light-transmissive body 32 and the light-transmissive layer 6, and is made to strike the test paper 8. Then, reflected light from the reagent layer (test paper) 8 reaches the photosensor 30b disposed at a position forming an angle of approximately 45° with respect to the incident light. As a result, the reaction color of the test paper 8 is read out, and the blood sugar value of the blood is determined on the basis of this reaction color.

The amount of time required for blood to infiltrate in the reagent layer 8 through the liquid development layer 10 and then to react after blood was applied it takes about one minute. Hence, in this automatic blood sugar measuring device 50, after blood is applied to the test piece 1, measurements are made after one minute has elapsed since the test piece 1 was inserted and loaded in the opening 24. In FIG. 4, numeral 2 denotes the main body of the test piece 1. [Explanation of the operation of the automatic blood sugar measuring device (FIGS. 1 to 6)]

Figure 5A:
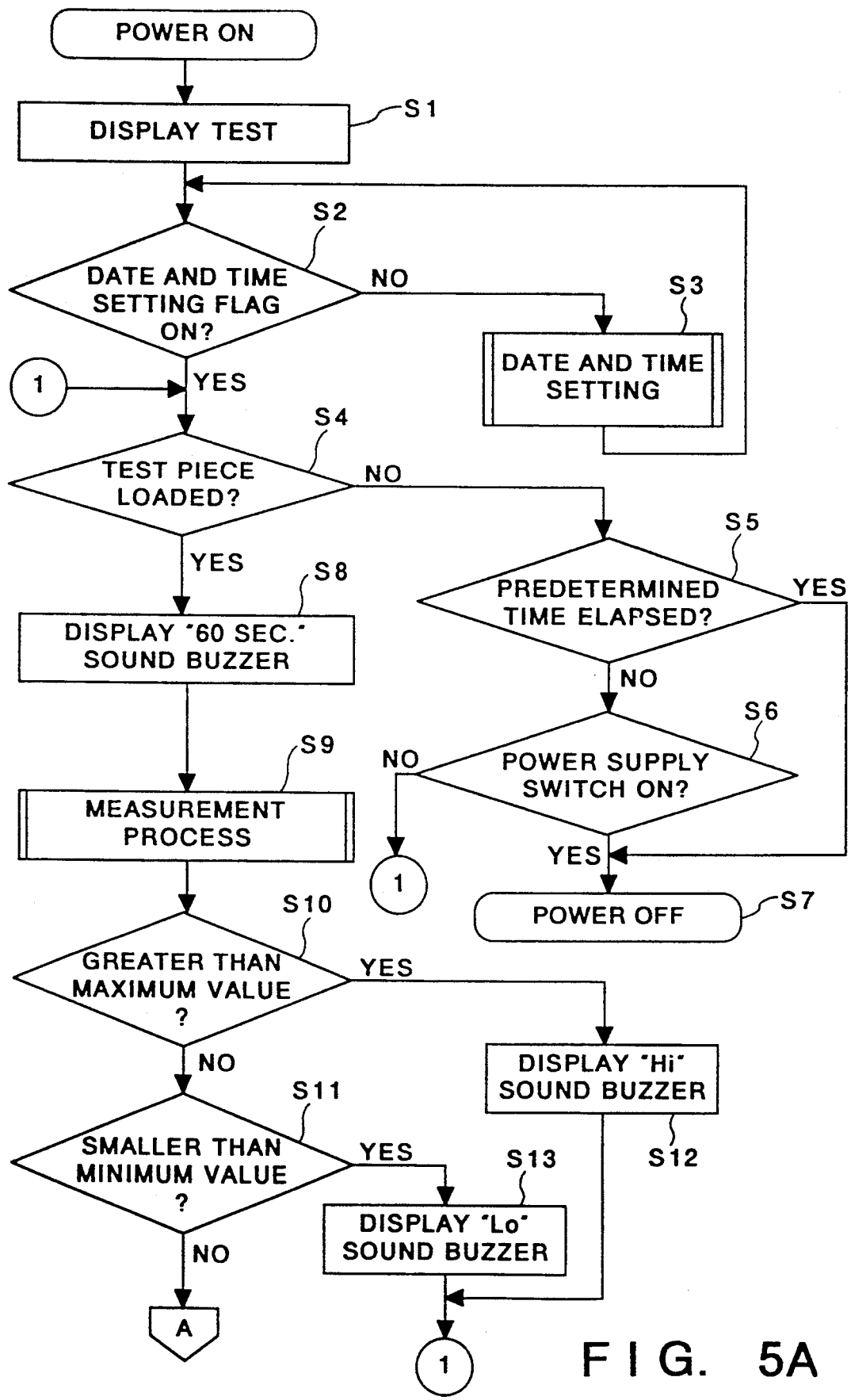
FIGS. 5A and 5B are flowcharts illustrating the measurement process in the blood sugar measuring device of the embodiment.
Figure 5B:
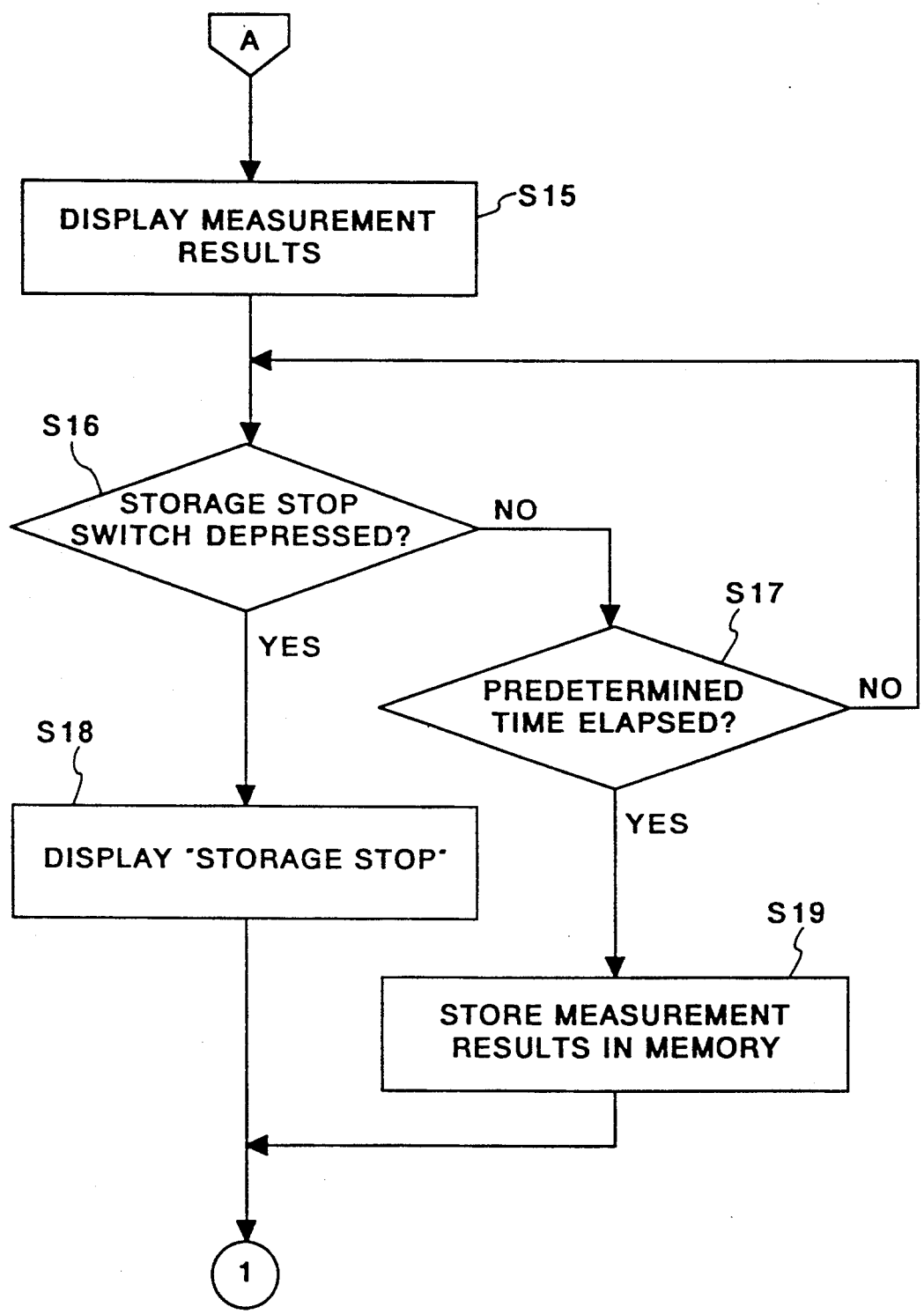

FIGS. 5A and 5B are flowcharts illustrating the operations in the blood sugar measuring device 50 of the embodiment. Control programs by which these operations are performed are stored in the ROM 73.

The operations shown in FIG. 5 are started as the result of the power supply of the device being turned on due to the power supply switch 52 of the device 50 being depressed. First, in step S1, in order to confirm whether or not the display section 51 is functioning normally, all items which can be displayed are displayed on the display section 51 for several minutes. Next, the process proceeds to step S2 where it is checked whether or not a day and time setting flag 74a of the RAM 74 is on. This flag 74a is turned on when a day and time data is set once and thereafter will not be turned off until all information is erased by an unillustrated all-clear switch.

Figure 6:
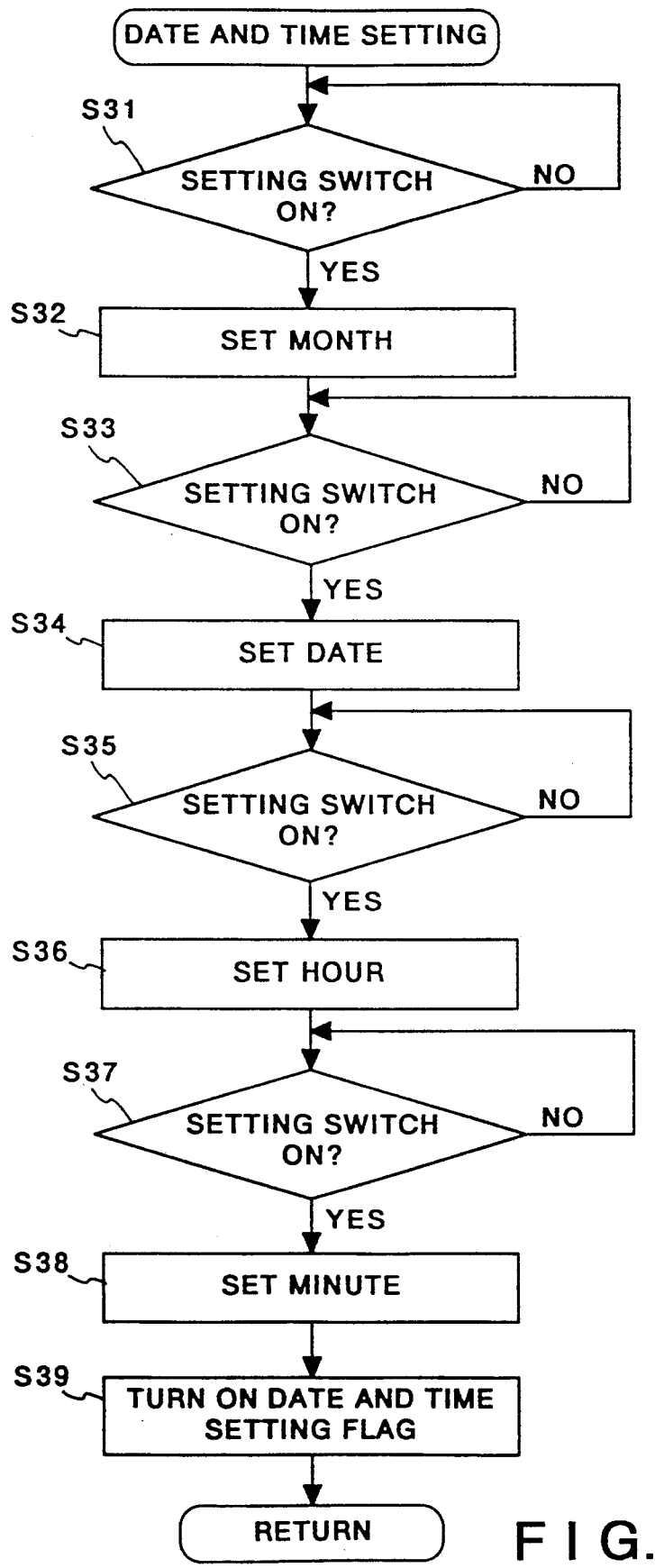
FIG. 6 is a flowchart illustrating a day and time setting process.

When the day and time data has not been set, the process proceeds to step S3 where the operation for setting day and time data shown by the flowchart of FIG. 6 is performed.

When the day and time data has been set (the flag 74a is on), the process proceeds to step S4 where whether or not the test piece 1 has been loaded is checked by determining whether or not the switch 36 is on. If the switch 36 is not on (the test piece 1 has not been loaded), the process proceeds to step S5 where it is checked whether or not a predetermined time period (for example, five minutes) has elapsed. If the predetermined time period has elapsed, the process proceeds to step S7 where the power supply of the device 50 is turned off. If the predetermined time period has not yet elapsed in step S5, the process proceeds to step S6 where it is checked whether or not the power supply switch 52 has been depressed. When yes, the process proceeds to step S7 where the power supply of the device 50 is turned off. In the power-off state of step S7, the display section 51 is erased only. Since power is supplied to both the RAM 74 and the control section 70, the contents of the RAM 74 will be maintained.

When it has been detected in step S4 that the test piece 1 has been loaded, the process proceeds to step S8 where "60" seconds is displayed on the display section 51, and in step S9, an operation for measuring blood sugar is performed. This operation will be described later in detail with reference to the flowchart of FIG. 7.

When the blood sugar value has been determined in step S9, the process proceeds to step S10 where it is checked whether or not the measurement result is greater than an allowable maximum value. If the result is smaller than the allowable maximum value, the process proceeds to step S11 where the result is compared with an allowable minimum value. If the measurement result is between the allowable maximum value and the allowable minimum value, the process proceeds to step S15 where the measurement result is displayed on the display section 51. At this time, if the measured value is smaller than the allowable minimum value, "Lo" is displayed on the display section 51 in step S13; if greater than the allowable maximum value, "Hi" is displayed in step S12, thus notifying an operator of the fact that the measured value is abnormal.

If the measured value is within the allowable range, whether or not the storage stop switch 54 described above has been depressed within a predetermined time period (about 3 min.) in steps S16 and S17 is determined. If the switch 54 is not depressed within the predetermined time period, the process proceeds to step S19 where the measurement result is stored in the RAM 74 along with the current day and time information. If the storage stop switch 54 is depressed within the predetermined time period, the process proceeds to step S18 where the fact that storage is stopped is displayed on the display section 51 and then the process returns to step S4.

FIG. 6 is a flowchart illustrating the day and time setting process of step S3 of FIG. 5.

In step S31, the system waits for the setting switch 55 to be depressed. If it is depressed, the process proceeds to step S32 of a month data update process, in which month data blinks on and off and month data is increased by 1 each time the change switch 56 is depressed. When the month becomes the month which it is desired to set in this manner, the setting switch 55 is depressed. As a result, month data which is currently displayed on the display section 51 is stored as month data in the RAM 74.

Hereinafter, in the same way as the above, when the setting switch 55 is turned on in step S33, day data is made to blink on and off and is displayed. In step S34, day data set by means of the change switch 56 is set by the setting switch 55. Similarly, hour data is set in steps S35 and S36, and minute data is set in steps S37 and S38. When month, day, and hour data are set in this manner, the day and time setting flag 74a is set in step S39.

The day and time data which has been set in the above way is updated at all times according to the information from the timer 78. When the blood sugar value is measured, the result of the measurement is stored in the memory (the RAM 74) together with the day and time data. Whenever the storage retrieval switch is depressed, the measurement result can be read out and displayed on the display section 51 along with the stored day and time data. [Explanation of the measurement process (FIGS. 7 and 8)]

Figure 7:
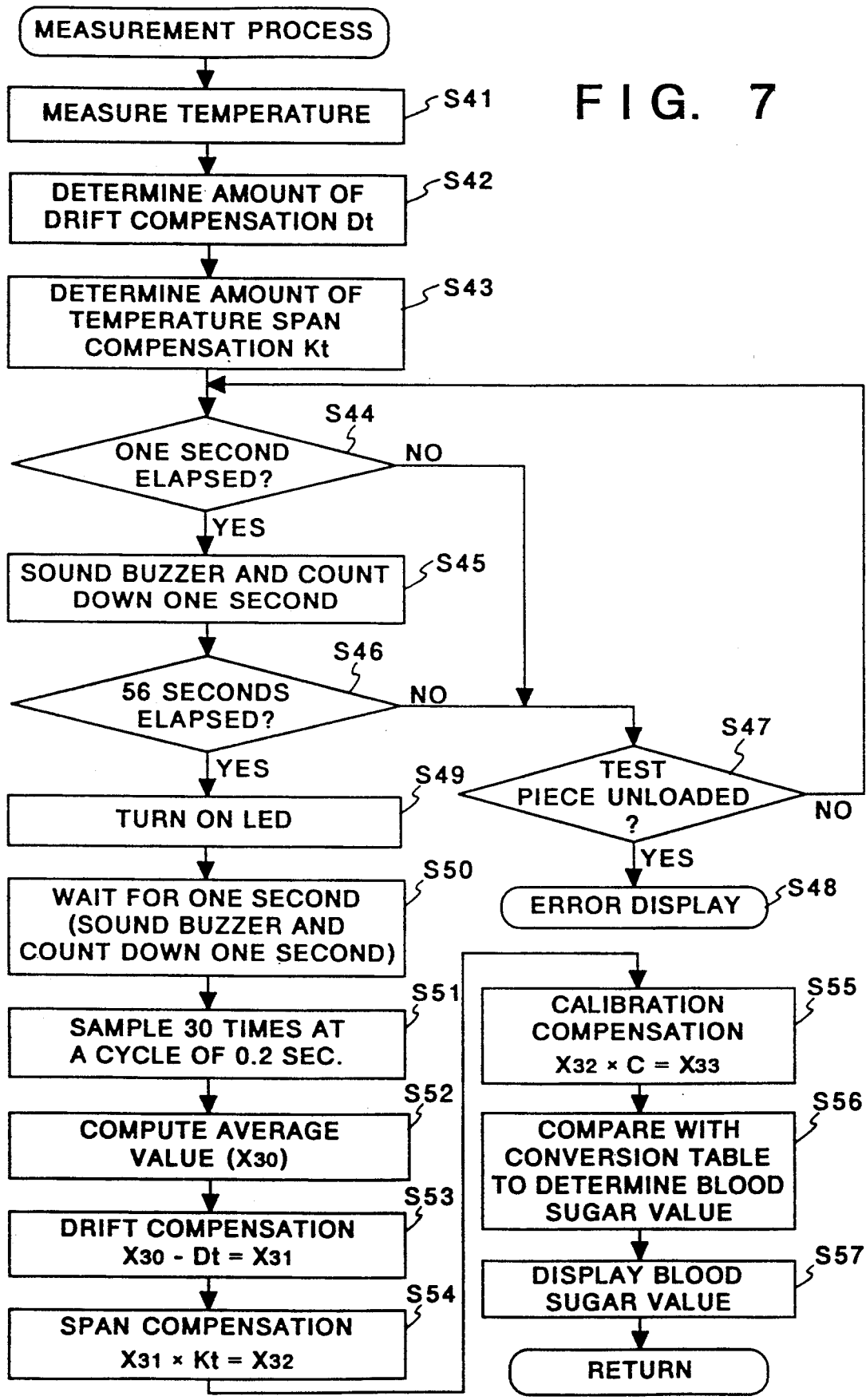
FIG. 7 is a flowchart illustrating the details of the measurement process.

FIG. 7 is a flowchart illustrating the procedure of the measurement process of step S9 of FIG. 5.

In step S41, temperature data from the temperature sensor 80 is entered in order to obtain an ambient temperature in which the device 50 is placed. In step S42, temperature drift data Dt corresponding to the temperature is obtained by referring to the table 73a stored in the ROM 73 on the basis of the temperature data. Next, in step S43, a temperature span compensation amount Kt is determined by referring to another table 73b in the ROM 73, on the basis of the above temperature data. In steps S44 to S45, the buzzer 79 is made to sound each time one second has elapsed, and the display on the display section 51 is counted down and displayed.

In step S46, whether or not 56 seconds have elapsed is checked. When not elapsed, whether or not the test piece 1 is unloaded is checked in step S47. When unloaded, an error message "Err" is displayed on the display section 51 in step S48, and the process returns to step S4. The detection of whether or not the test piece 1 is unloaded is performed concurrently in steps S49 to S51 which will be described later—this fact is not shown in the flowchart of FIG. 7. When the test piece 1 is unloaded from the device 50 during these operations, the measurement process is immediately stopped and an error message is displayed.

When 56 seconds have elapsed in step S46, the process proceeds to step S49 where the LED 30a is caused to emit light, and power is supplied to an analog circuit (the signal detection circuit 76) for detecting a signal from the photosensor 30b. In step S50, the system waits for approximately one second until the output of the LED 30a and the analog circuit 76 are stabilized. In the subsequent steps, the buzzer 79 sounds and the count-down for every second is displayed. This operation is performed until one minute has elapsed from the time the test piece 1 is loaded. Next, in step S51, signals from the photosensor 30b are sampled 30 times in six seconds (once every 0.2 seconds) and after these signals are converted into digital signals by means of the A/D converter 81, they are input. As a result, a measurement is started at 57 seconds after the test piece 1 is loaded, and this measurement continues up to 63 seconds. At the termination of the 60 second measurement period, the count-down display on the display section 51 is stopped.

In step S52, the sum of the measured values of the 30 signal samples of step S51 is computed. By dividing the sum value by "30", an average value ($X_{30}$) is determined. It is considered that this average value ($X_{30}$) indicates an average measurement value during the time period spanning 3 seconds before and 3 seconds after the elapse of the reference time of exactly one minute.

Figure 8:
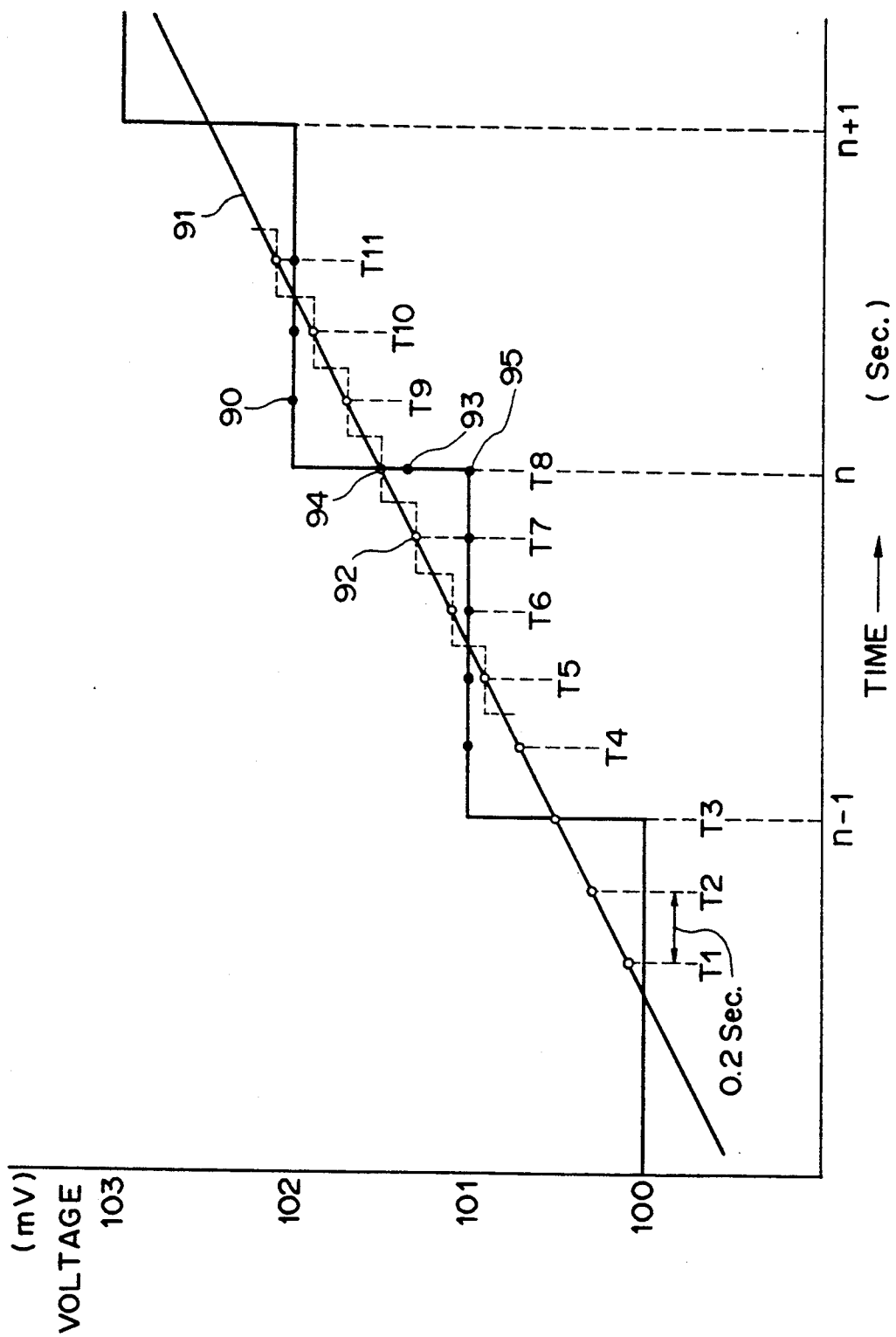
FIG. 8 is a view for explaining digital conversion discrepancies with respect to reflected light intensity which changes almost linearly.

FIG. 8 is a view showing the case where two voltage values are compared to each other. The first voltage is a true voltage value, which is detected and output by means of the photosensor 30b, and the second voltage value is that which is converted from analog to digital by means of the A/D converter 81. It is supposed that the aforesaid true voltage value changes uniformly upwardly or downwardly during a sampling period.

In FIG. 8, numeral 90 denotes a signal in which a true output voltage 91 from the photosensor 30b is sampled at an interval of one second, and is converted to a digital value. T1 to T11 denote sampling timings (at an interval of 0.2 seconds) in this embodiment. The black circles "●" shown in FIG. 8 denote digital read-out values containing A/D conversion discrepancies. At this point, for example, digital read-out values in the timings T5 to T11 are added, and it is divided by the number of samplings (7 times) to determine an average value, which becomes a value shown by 93 in FIG. 8. Compared with the one-time digital read-out value shown by 95 as timing T8, this value is nearer to the true value 0 of the analog voltage in timing T8. As described above, by obtaining the average of a plurality of sampling values before and after a time at which a measurement is desired, A/D conversion discrepancies can be diminished.

When the measurement value (the average value ($X_{30}$)) after one minute from the time the test piece 1 is loaded into the device 50 is obtained in the above way, the process proceeds to step S53 where the drift value (Dt) obtained in step S42 is subtracted from the average value $X_{30}$. That value is then multiplied by the span compensation amount (Kt) in step S54 so that a temperature compensation is made on the obtained average value.

An average value $X_{32}$ on which temperature compensation has been made is multiplied by a coefficient C, furthering the calibration compensation. The initial value of this coefficient C is "1". It can take any value between 0.90 and 1.10, depending on preliminary tests. Next, the process proceeds to step S56, where a blood sugar value is determined by referring to a conversion table 73c stored in the ROM 73 on the basis of these compensated values, and the blood sugar value is displayed on the display section 51.

As has been explained above, according to this embodiment, an analog signal indicating a reflected light intensity is sampled at a short interval and digitized, thus a value close to an actual reflected light intensity can be obtained.

A plurality of data before and after the measurement time (timing) are sampled, and an average value of these is calculated. As a result of this averaging, an accurate measurement value at the timing when a measurement is desired, can be obtained.

In this embodiment, the example of a blood sugar measuring device is explained. However, the present invention is not limited to this device. It is needless to say that it can be applied to, for instance, an analysis device for uric acids, GTO, GPT, cholesterol, or the like. Regarding a specimen, for example, body fluids such as urine and saliva may be used.

As many widely different embodiments of the present invention can be made without departing from the spirit and scope thereof, it is to be understood that the invention is not limited to the specific embodiments thereof except as defined in the appended claims.

What is claimed is:

1. A measuring apparatus adapted to receive a test piece, to which a specimen is applied, that measures a concentration of the specimen on the basis of a change of color of a test material which is housed in said test piece and which reacts with said specimen, comprising:
    irradiation means for irradiating said test material with light;
    loading detection means for detecting whether the test piece is inserted into a main body of the apparatus;
    time measurement means for measuring a predetermined time period in which the reaction of said test material with the specimen is substantially completed, after the insertion of said test piece is detected by means of said loading detecting means;
    detection means for detecting an intensity of the light reflected from said test material and outputting a corresponding analog signal;
    digital conversion means for sampling said analog signal a plurality of times before and after the predetermined time period has elapsed and converting each sample into a digital signal; and
    computation means for computing an average value of said digital signals sampled by said digital conversion means and determining the constituent concentration of said specimen by referring to a stored conversion table on the basis of said average value.

2. The measuring apparatus according to claim 1, further comprising temperature measurement means for measuring ambient temperature in which the apparatus is placed and correcting means for correcting said average value on the basis of said ambient temperature.

3. The measuring apparatus according to claim 1, further comprising display means for displaying the time measured by said time measurement means, by means of a count down on a display screen.

4. The measuring apparatus according to claim 1, further comprising storage means for storing the constituent concentration of said specimen together with the day and time of measurement; and
    selection means for automatically selecting whether or not said constituent concentration is stored in said storage means.

5. The measuring apparatus according to claim 1, further comprising temperature measurement means for measuring ambient temperature in which the apparatus is placed and correcting means for correcting said average value on the basis of said ambient temperature, and display means for displaying the time measured by said time measurement means, by means of a count down on a display screen.

6. The measuring apparatus according to claim 1, wherein said test piece is provided with a first opening on one side thereof and a second opening on another side thereof at a location opposite to said first opening, said first opening provided for applying the specimen to said test material therethrough, sand said second opening for irradiating said test material with the light and detecting the intensity of the reflected light therefrom.

7. A measuring apparatus adapted to receive a test piece, to which a specimen is applied, that measures a concentration of the specimen on the basis of a change of color of a test material which is housed in said test piece and which reacts with said specimen, comprising:
    loading detection means for detecting whether the test piece is inserted into a main body of said apparatus;
    time measurement means for measuring a predetermined time period in which the reaction of said test material with the specimen is substantially completed, after the insertion of said test piece is detected by means of said loading detection means;
    irradiation means for irradiating said test material with light before and after the predetermined time period has elapsed;
    detection means for detecting an intensity of light reflected from said test material irradiated by said irradiation means and outputting a corresponding analog signal;
    digital conversion means for sampling said analog signal a plurality of times before and after said predetermined time period has elapsed and converting each sample into a digital signal;
    computation means for computing an average measurement value by computing the average value of said digital signals sampled by said digital conversion means; and
    arithmetic operation means for determining the constituent concentration of said specimen by referring to a stored conversion table on the basis of said average measurement value.

8. The measuring apparatus according to claim 7, further comprising temperature measurement means for measuring ambient temperature in which the apparatus is placed and correcting means for correcting said average value on the basis of said ambient temperature.

9. The measuring apparatus according to claim 7, further comprising display means which displays a lapse of the predetermined time period on a display screen at predetermined time intervals by means of counting down after the loading of said test piece is detected by means of said loading detection means.

10. The measuring apparatus according to claim 7, further comprising storage means for storing the constituent concentration of said specimen together with measurement day and time data; and
    selection means for automatically selecting whether or not said constituent concentration is stored in said storage means.

11. The measuring apparatus according to claim 6, wherein said test material includes a liquid development layer in which said specimen is infiltrated through said first opening, a reagent layer which reacts with said specimen and a transparent layer between the reagent layer and the second opening, and said predetermined time period is defined by the time in which the coloring reaction between said specimen infiltrated through the liquid developing layer and said reagent layer is substantially completed.

12. The measuring apparatus according to claim 7, further comprising temperature measurement means for measuring ambient temperature in which the apparatus is placed and correcting means for correcting said average value on the basis of said ambient temperature, and display means for displaying the time measured by said time measurement means, by means of a count down on a display screen.

13. The measuring apparatus according to claim 7, wherein said test piece is provided with a first opening on one side thereof and a second opening on another side thereof at a location opposite to said first opening, said first opening provided for applying the specimen to said test material therethrough, and said second opening for irradiating said test material with the light and detecting the intensity of the reflected light therefrom.

14. The measuring apparatus according to claim 13, wherein said test material includes a liquid development layer in which said specimen is infiltrated through said first opening, a reagent layer which reacts with said specimen and a transparent layer between the reagent layer and the second opening, and said predetermined time period is defined by the time in which the coloring reaction between said specimen infiltrated through the liquid developing layer and said reagent layer is substantially completed.

* * * * *

UNITED STATES PATENT AND TRADEMARK OFFICE
CERTIFICATE OF CORRECTION

PATENT NO. : 5,231,576
DATED : July 27, 1993
INVENTOR(S) : Yoshiro SUZUKI et al

It is certified that error appears in the above-indentified patent and that said Letters Patent is hereby corrected as shown below:

In Column 8, line 30, delete "as" and insert -- at --.
In Column 9, line 65, delete "the" and insert -- a --.
In Column 9, line 66, delete "sand" and insert -- and --.
In Column 11, line 5, delete "the" and insert -- a --.

Signed and Sealed this

Fifth Day of April, 1994

Attest:

BRUCE LEHMAN

Attesting Officer

Commissioner of Patents and Trademarks